United States Patent [19]

Romero et al.

[11] Patent Number: 5,791,705
[45] Date of Patent: Aug. 11, 1998

[54] TOOL HOLDING APPARATUS FOR PERSONS WITH LIMITED USE OF HANDS

[76] Inventors: Ramiro Roy Romero, 219 Ellingbrook Dr., Montebello, Calif. 90640; Cynthia Marie Deslarzes, 29239 Heather Cliff, #8, Malibu, Calif. 90265; Ron Anson, 414 S. Cliffwood La., Los Angeles, Calif. 90049

[21] Appl. No.: 708,192

[22] Filed: Sep. 6, 1996

[51] Int. Cl.⁶ .................... A45F 5/00; A61F 2/54
[52] U.S. Cl. ............... 294/25; 30/298; 224/218; 401/8
[58] Field of Search ............. 294/1.1, 25; 15/437, 15/443; 30/298; 224/218, 219, 222, 267; 401/8; 623/65

[56] References Cited

U.S. PATENT DOCUMENTS

| | | | |
|---|---|---|---|
| 426,324 | 4/1890 | Ramsey | 401/8 X |
| 816,286 | 3/1906 | Akin | 30/298 X |
| 828,798 | 8/1906 | Anderson | 30/298 X |
| 1,181,527 | 5/1916 | Hooper | 30/298 |
| 1,403,002 | 1/1922 | Barns | 30/298 X |
| 2,501,552 | 3/1950 | Thompson | 401/8 |
| 3,503,546 | 3/1970 | Hunt | 224/218 |
| 4,165,896 | 8/1979 | Hunt | 294/25 |
| 4,602,885 | 7/1986 | Bischoff et al. | 294/25 X |
| 4,606,484 | 8/1986 | Winter et al. | 294/25 X |
| 5,597,891 | 1/1997 | Barbee | 294/25 |

*Primary Examiner*—Johnny D. Cherry

[57] ABSTRACT

An improved apparatus to assist in gripping a hand-held tool is adapted to be easily coupled to one's hand. A hand engaging portion for removably engaging a portion of a palm and a portion of a back of a hand is provided. A tool receiving portion is coupled to the hand engaging portion and receives the hand-held tool. A band for securing the hand-held tool to the tool receiving portion is also provided. The hand engaging portion defines at least one groove for receiving the band for securing.

5 Claims, 2 Drawing Sheets

TOOL HOLDING APPARATUS FOR PERSONS WITH LIMITED USE OF HANDS

BACKGROUND OF THE INVENTION

1. Field of the Invention

This invention relates to an apparatus designed to assist persons with limited gripping ability to use hand-held tools.

2. Description of the Related Art

In the prior art, there are many devices that are designed to assist one in gripping a hand-held tool.

One example of such a device is described in U.S. Pat. No. 4,606,484 (hereinafter referred to as the Winter reference). The Winter reference discloses a tool holding device having a rotatable resilient center with an integral socket to receive tools that are specifically shaped to fit in the socket. The Winter device employs a strap to couple the socket to one's hand. However, this prior art device has several disadvantages. First, it is difficult, even for one of average dexterity, to attach the Winter device to one's hand. One must thread a strap through a D-ring to affix the Winter device to one's hand. This difficulty is magnified for one having limited hand dexterity. In fact, one with limited hand dexterity would most likely require assistance from a third person to attach the Winter device to one's hand.

The other prior art devices known to applicant that employ a more rigid (less flexible) loop or clip to attach the device to one's hand are also difficult to couple to one's hand because they enclose substantially all of the back of one's hand and one's palm. Devices that employ a wire-like material to wrap around one's hand are also relatively difficult to attach and disengage from one's hand because additional bending and flexing of the wire-like material is required.

The prior art devices employing a clip that attaches to one's hand also suffer from the disadvantage that they employ pockets made of a cloth or leather material that are difficult to clean, susceptible to harbor germs and bacteria, and raises sanitary issues that may jeopardize the health and safety of the user. Moreover, the pockets made of the clothlike material are very limited in terms of the size of the tools which may be accommodated.

A second disadvantage of the Winter device is that it can only accommodate those tools which have a handle specifically designed and shaped for use with the Winter socket. This severely limits the type of tools available to the user to those manufactured particularly for the Winter device. As a result, purchasing additional tools are costly, difficult to obtain, and wasteful of tools currently in one's possession.

Other prior art devices also have the disadvantage of not being able to accommodate a wide variety of tools and accessories. For example, prior art devices are often designed and manufactured for one use or a small limited number of uses and cannot be used with other tools. As mentioned previously, the devices that employ "pockets" can accommodate only a very small slight variation in the size of a tool's handle. For example, while a pocket may accommodate eating utensils such as a spoon, and fork, the same pocket could not be used to hold a hairbrush having a handle with a larger diameter.

The third disadvantage of the Winter device is that although the device offers rotation of a utensil, this rotation comes at the expense of increased complexity of design which leads to increased manufacturing costs, and maintenance cost associated with the device.

SUMMARY OF THE INVENTION

The improved apparatus to assist in gripping a hand-held tool includes a hand engaging portion for removably engaging a hand, a tool receiving portion, coupled to the hand engaging portion, for receiving the hand-held tool and means for securing the tool to the tool receiving portion.

In a first embodiment, the hand-engaging portion is formed integrally with the tool receiving portion. The improved apparatus engages a portion of the back of the hand, wraps around and engages the entire length of the palm, and extends beyond the palm. The portion of the improved apparatus extending beyond the palm defines at least one groove for receiving a means for securing the tool to the tool receiving portion. The means for securing are elastic bands that may be of different sizes to accommodate utensils having handles of different sizes.

The improved apparatus is formed from a substantially rigid material (e.g., plastic) that allows the hand engaging portion to easily engage and disengage from a hand without the use of the other hand (i.e., the improved apparatus offers "one hand operation"). This "one hand operation" allows the user to engage the improved tool gripping device comprising the present invention to one's hand by employing only the hand to which the improved tool gripping apparatus is to be coupled and a surface.

For example, this surface may be the top surface of a table or a counter. To engage the device, one simply aligns the side portion of one's palm (e.g., the portion that extends from the little finger) and brings that portion of the hand into the hand engaging portion of the apparatus by applying a slight pressure. Once engaged, the hand engaging portion grips the palm and in effect "clips" onto that portion of the palm. Even a person without grip strength and without finger mobility can readily "clip" the apparatus to their hand with ease.

Furthermore, this improved apparatus is simple yet elegant in design, and lightweight, making both the manufacture and maintenance of this improved apparatus very cost effective. Moreover, parts such as the means for securing (e.g., O-rings) may easily be replaced and elastic bands of different sizes are readily available in the marketplace. The design of this improved apparatus also has sanitation issues in mind in that all parts are easily washable and are dishwasher safe. Moreover, all components do not contain cloth and/or leatherlike materials that may harbor germs and bacteria, as in the prior art.

In a second embodiment, the tool receiving portion includes a surface that substantially encloses a handle of the hand-held tool. The tool receiving portion defines this elongate enclosure. However, this enclosure includes a groove through which the hand-held tool may be placed into and removed from the elongate enclosure. The tool fits snugly in the tool receiving portion, but may be removed from said portion with a slight force. In this embodiment, one means for securing is employed. For tools such as a knife, where additional force is exerted on the tool, this embodiment provides additional support for the tool for one with limited hand movement.

In a third embodiment, the improved tool is adapted specifically for holding a cup. The means for securing the tool includes a hook member and support boss that are disposed to hold the cup. Applicant is unaware of any prior art that provides an apparatus assisting those limited in hand movement with cups.

In the fourth embodiment, the tool receiving portion is rotatably coupled to the hand engaging portion via means for coupling (e.g., threaded nut and bolt, rivet, etc.). This embodiment of the improved apparatus allows rotation of the tool receiving portion about the hand engaging portion. This simple and elegant design allows a user greater flexibility in employing tools that may require limited rotation. These tools may include writing utensils, a toothbrush, typing instrument, and eating utensils (e.g., spoon and fork). The manufacturing costs, replacement costs, and maintenance costs of this improved apparatus are all significantly lower than those noted in the prior art because of the improved apparatus's simple yet elegant design. Moreover, this apparatus, as in the other embodiments, is adapted to easily engage and disengage from one's hand with minimal effort.

BRIEF DESCRIPTION OF THE DRAWINGS

The objects, features and advantages of the method and apparatus for the present invention will be apparent from the following description in which.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structures. The scope of the invention is defined in the claims appended hereto. The basic form of the invention is shown in FIGS. 1-7.

It should be noted that the hand shown in the figures is shown very sketchily and in phantom because they may represent either the back of the hand, the palm of the hand and may also represent either hand. Although the device is shown mounted on a hand, it may also be mounted across the knuckles of the hand or if the individual lacks effective hands, it may be mounted on a portion of one's arm. If the person lacks effective arms and has sufficient leg mobility, it is even possible to modify the hand engaging portion of this device so as to be adapted to couple to one's leg.

It should also be noted that the term "tool" encompasses a wide variety of devices. Although the figures show a comb, knife, cup and pen, these devices are merely illustrative of an unlimited range of tools that may be held by the present invention. For example, a tool may include, inter alia, an eating utensil (e.g., fork, spoon, knife), a shaving utensil (e.g., razor), a hairbrush, a comb, a toothbrush, a cup, a typing instrument (employed for manipulating a keyboard or a typewriter), a writing utensil (e.g., pen, pencil) and other tools used in life.

Figure 1:
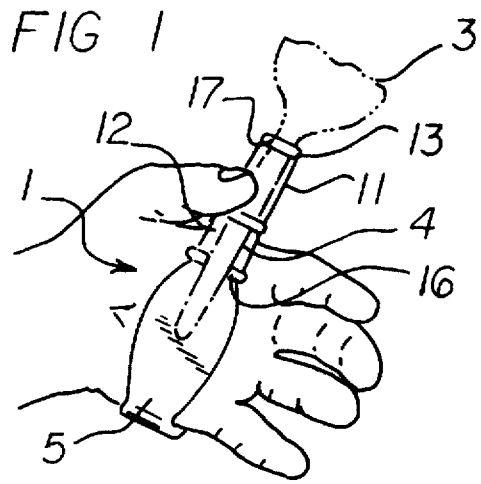
FIGS. 1 and 2 illustrate perspective views of one embodiment of the present invention.
Figure 2:
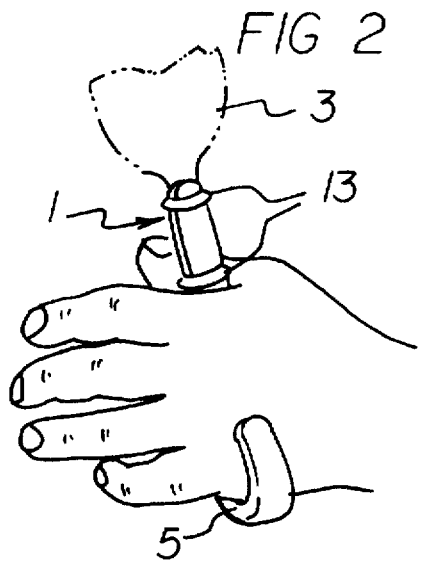
Figure 5:
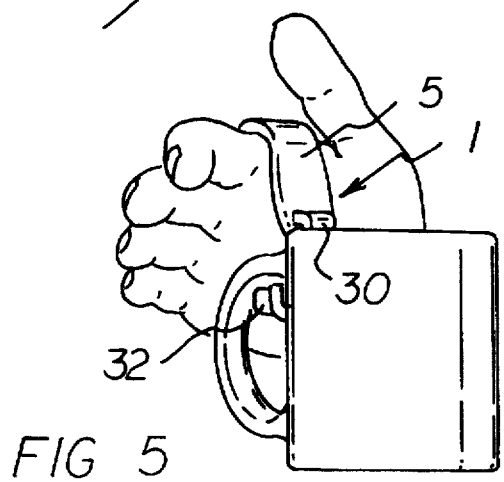
FIG. 5 illustrates a perspective view of a third embodiment of the present invention that is adapted to aid one in the utilization of a cup.
Figure 6:
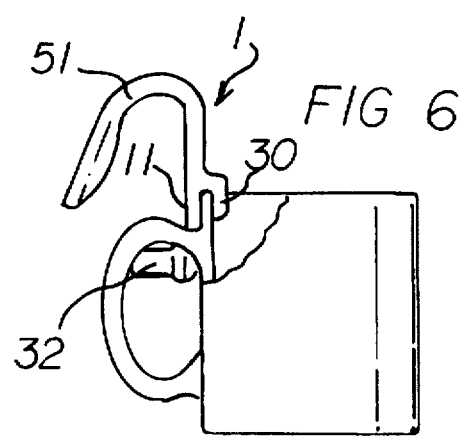
FIG. 6 illustrates a side elevation view of how the third embodiment of the present invention attaches to the cup.

FIGS. 1 and 2 illustrate perspective views of one embodiment of the present invention. The apparatus 1, to assist in gripping a hand-held tool, includes a hand engaging portion 5 coupled to a tool receiving portion 11. The hand engaging portion 5 is configured to simultaneously engage at least a portion of a palm of hand and a back of the hand. As shown in the Figures, the hand engaging portion has a first linear member with a first surface and a second linear member with a second surface to simultaneously engage a portion of the palm of the hand and a portion of the back of the hand, respectively. The linear members remain in parallel relationship along an entire extent thereof and the second linear member is equipped with a free second end. By sliding one's hand into the engaging portion 5 and applying slight pressure so that the engaging portion grips the side portion of the palm extending from the little finger, the improved tool gripping apparatus 1 comprising the present invention easily engages and disengages from a hand with minimal effort. In fact, the hand engaging portion 5 "clips" to the user's hand and may be coupled to the user's hand with minimal effort even for one with limited hand movement. It will be understood by those skilled in the art that the embodiments shown in FIGS. 1, 2, 3, 4, and 7-9 may be adapted accordingly so as to have the hand engaging portion receive ("clip to") the portion of the hand between the thumb and index finger as illustrated in FIGS. 5 and 6.

The apparatus 1 may be manufactured by employing a substantially rigid material (e.g., plastic) that is flexible, yet durable. Conventional manufacturing techniques, such as injection molding and other molding techniques, may be employed to make the tool gripping apparatus 1. It is preferred that the material used to make the improved gripping apparatus 1 be moldable and formable by the application of heat to the material (e.g., with a heat gun or boiling water). Such moldable and formable material allows the hand engaging portion 5 to be modified by the application of heat so as to enable the hand engaging portion 5 to be adapted to fit snugly the hand of a user.

The tool receiving portion 11 is adapted to receive any number of different tools 3. This tool 3 typically includes a handle 4. As show in the Figures, the tool receiving portion is coupled to a second end of the first linear member of the hand engaging portion. The tool receiving portion 11 includes a surface 12 for engaging said handle 4 of said tool. The present invention 1 also includes means 13 for removably securing the tool 3 to the tool receiving portion 11. In the preferred embodiment, the means for securing 13 are elastic bands (e.g., O-rings). However, it will be understood by those skilled in the art that other conventional means for securing may be employed. It should be noted that different sized O-rings may be employed to accommodate different tools 3 with different handle sizes and shapes. For example, an O-ring of a first size may be employed to couple the present invention 1 to a comb 3 that has a handle with a relatively small diameter. An O-ring of a second size is employed to couple the present invention 1 to a hairbrush 3 having a handle with a larger diameter.

The tool receiving portion 11 further defines an extension of the first linear member and at least one groove 16 for receiving said means for securing 13. In a preferred embodiment, the tool receiving portion 11 defines at least two grooves (16, 17) for receiving two means for securing 13.

In the preferred embodiment, the hand engaging portion 11 engages the back of a hand, wraps around and extends across a portion of a palm of the hand. The tool receiving portion 11 extends across a portion of the palm and beyond the palm. The tool receiving portion 11 that extends beyond the palm defines at least one groove (16) for receiving the means for securing 13. Other portions of the tool receiving portion 11 also may define a groove for receiving means for securing 13.

Figure 3:
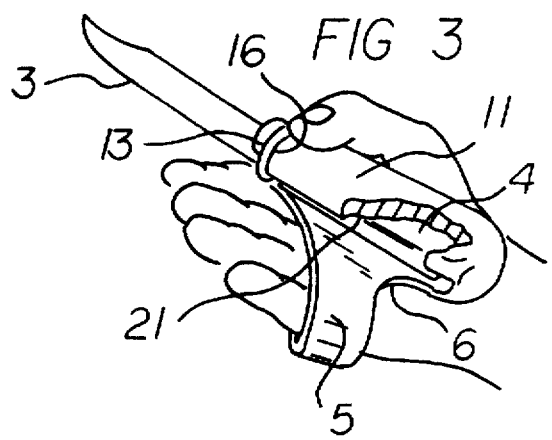
FIGS. 3 and 4 illustrate perspective views of an alternative embodiment of the present invention.
Figure 4:
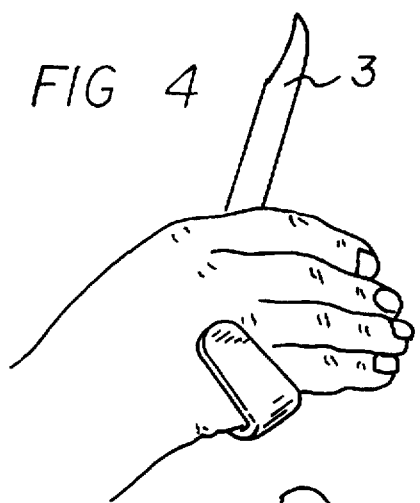

FIGS. 3 and 4 illustrate perspective views of an alternative embodiment of the present invention. In this embodiment, the hand engaging portion 5 includes a first surface 6 for engaging the palm of the hand and a second surface 7 for engaging the back of the hand. The tool receiving portion 11 forms a surface that substantially encloses the handle 4 of a tool 3. The tool receiving portion 11 defines the surface in such a way as to snugly hold the handle of the tool. However, the tool receiving portion 11 includes a channel 21 through which the tool may be removed from or received by said tool receiving portion 11 with slight force/pressure. In this embodiment, the tool receiving portion 11 also defines a groove 16 for receiving the means for securing 13. For this embodiment, one means for securing (e.g., O-ring) 13 is employed. As shown in FIGS. 3 & 4, the tool receiving portion of the present embodiment is integrally coupled at a central extent thereof to a second end of the second linear member of the hand engaging portion such that the tool receiving member remains in coplanar relationship with the first linear member of the hand engaging portion and further defines an obtuse angle therewith.

FIG. 5 illustrates a perspective view of an alternative embodiment of the present invention that is adapted to hold a cup. FIG. 6 illustrates a side elevational view of how the third embodiment of the present invention attaches to the cup. The present invention 1 includes the hand engaging portion 5 and the tool receiving portion 11. The means for securing 13 include a first flange 30 (i.e., a hook member) and a second flange 32 (i.e., a support protrusion or boss) that are disposed to hold said cup. In the preferred embodiment, the hook member 30 engages a rim of the cup, and the support boss 32 (i.e., a support protection or bass) engages the handle of the cup. In the preferred embodiment, the hook member 30 and the support boss 32 are integrally molded with said tool receiving portion 11. To attach this embodiment of the present invention to a cup, one simply engages the hook member 30 to a position along the rim of the cup that is slightly offset from a position on the rim directly above the handle of the cup. One then positions the support boss 32 so that it engages the handle of the cup as it is moved into the aperture of the cup handle. FIG. 6 illustrates a side of the elevational view of how the third embodiment of the present invention attaches to the cup. The hook portion 30 and the support boss 32 are disposed to hold the cup and to prevent the cup from rotating away from the present invention.

This embodiment of the present invention is formed in an advantageous way so that the sides of the cup do not contact the hand. This is particularly advantageous for those persons having limited grip ability, whose skin in the palm is typically more sensitive than that of the average person. In this embodiment, although the palm comes in contact with the cup handle, it is not in direct contact with the sides of the cup, thereby preventing burning of the sensitive skin of the palm of such users.

Figure 7:
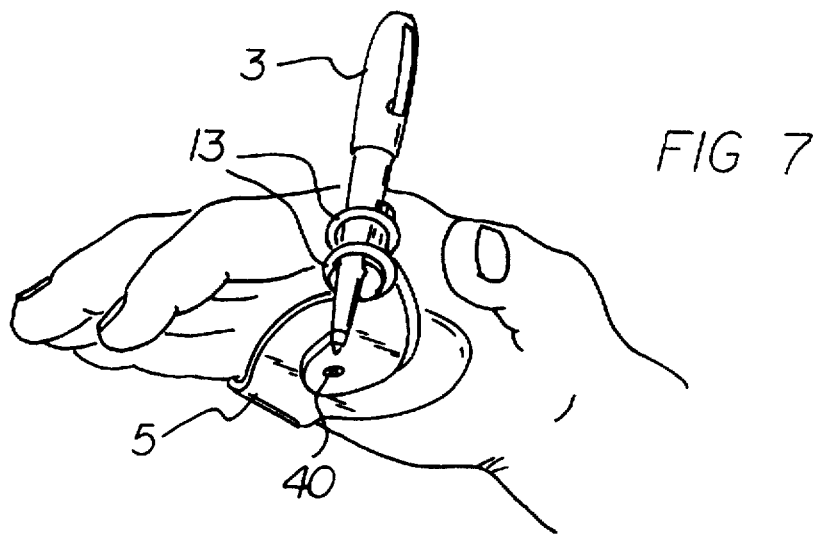
FIG. 7 illustrates a perspective view of a fourth embodiment of the present invention.
Figure 8:
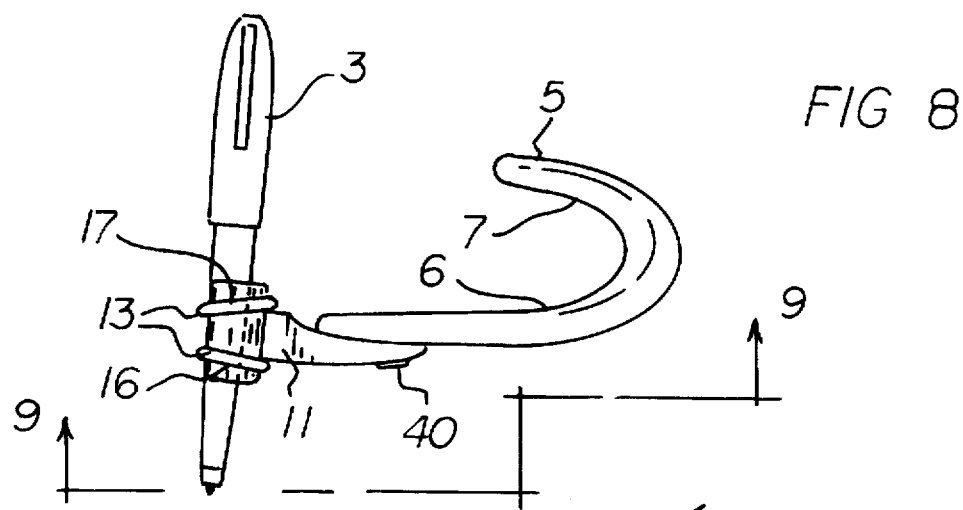
FIG. 8 illustrates a side elevational view of the fourth embodiment of the present invention.
Figure 9:
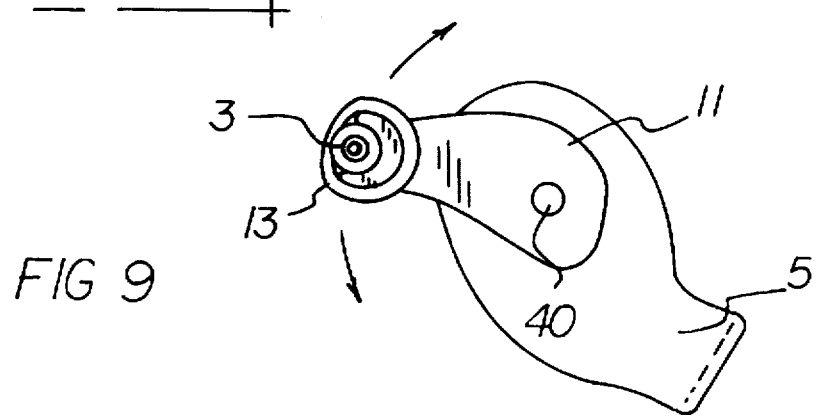
FIG. 9 illustrates a bottom plan view of the fourth embodiment of the present invention taken generally through line 9—9 of FIG. 8.

FIG. 7 illustrates a perspective view of a fourth embodiment of the present invention. FIG. 8 illustrates a side elevational view of the fourth embodiment of the present invention. FIG. 9 illustrates a bottom plan view of the fourth embodiment of the present invention taken generally through line 9—9 of FIG. 8. In contrast to the embodiment illustrated thus far in FIGS. 1–6, the tool receiving portion 11 is rotatably coupled to the first linear member of the hand engaging portion 5 instead of being integrally molded as one piece. The tool receiving portion 11 is rotatably coupled to the hand engaging portion 5 via coupling means 40 that are well known in the art (e.g., threaded nut and bolt, rivet, etc.). The means for coupling 40 should allow the tool receiving portion 11 to rotate. The tool receiving portion 11 in this embodiment, defines grooves (16, 17) for receiving the means for securing 13. Also, the tool receiving portion 11 defines a surface adapted to receive the tool. This embodiment is particularly useful for writing instruments, the typing instrument, a toothbrush, and eating utensils.

It will be noted by those skilled in the art, that the hand engaging portion 5 may be rotatably coupled to tool receiving portion 11 by properly injection molding the hand engaging portion with a hole disposed of approximately a quarter of an inch in diameter and three-quarters of an inch in depth, and by injection molding the tool receiving portion 11 with a stud of dimensions adapted to couple to the hole formed in the hand engaging portion 5.

What is claimed is:

1. An apparatus to assist in gripping a hand-held tool, said hand having a palm and a back, said apparatus comprising:

a) a substantially rigid hand engaging portion for removably engaging said hand; said hand engaging portion having a first linear member with a first surface and a second linear member with a second surface to simultaneously engage a portion of the palm of the hand and a portion of the back of the hand, respectively, wherein the first linear member has a first end connected to a first end of the second linear member such that the linear members are in parallel relationship along an entire extent thereof, the second linear member further having a free second end; wherein said hand engaging portion removably clips said apparatus to said hand;

b) a tool receiving portion including a closed bottom end and an open top end, the tool receiving portion integrally coupled at a central extent thereof to a second end of the first linear member of the hand engaging portion such that the tool receiving member remains in coplanar relationship with the first linear member of the hand engaging portion and further defining an obtuse angle therewith, the tool receiving portion having a portion extending beyond said hand, said tool receiving portion, coupled to said hand engaging portion, for receiving said tool; and c) means for securing said tool to said tool receiving portion including an elastic band;

wherein the portion extending beyond said hand of the tool receiving portion defines at least one concentric groove for receiving said elastic band;

wherein the tool receiving portion defines a surface, said surface substantially enclosing a handle of said tool, said tool receiving portion defining a linear channel through which said tool is placed into and taken out of said tool receiving portion.

2. An apparatus to assist in gripping a hand-held tool, said hand having a palm and a back, said apparatus comprising:

a) a substantially rigid hand engaging portion for removably engaging said hand; said hand engaging portion having a first linear member with a first surface and a second linear member with a second surface to simultaneously engage a portion of the palm of the hand and a portion of the back of the hand, respectively, wherein the first linear member has a first end connected to a first end of the second linear member such that the linear members are in parallel relationship along an entire extent thereof, the second linear member further having a free second end; wherein said hand engaging portion removably clips said apparatus to said hand;

b) a tool receiving portion coupled to a second end of the first linear member of the hand engaging portion such that the tool receiving member remains in coplanar relationship with the first linear member of the hand engaging portion, the tool receiving portion having a portion extending beyond said hand, said tool receiving portion, coupled to said hand engaging portion, for receiving said tool; and c) means for securing said tool to said tool receiving portion including an elastic band;

wherein the portion extending beyond said hand of the tool receiving portion defines at least one concentric groove for receiving said elastic band.

3. An apparatus as set forth in claim 2 wherein the tool receiving portion includes a channel for receiving the tool.

4. An apparatus as set forth in claim 2 wherein the tool receiving portion defines an extension of the first linear member of the hand engaging portion.

5. An apparatus as set forth in claim 2 wherein the tool receiving portion is rotatably coupled to the first linear member of the hand engaging portion.

* * * * *